United States Patent [19]

Flambard et al.

[11] 3,937,067
[45] Feb. 10, 1976

[54] MEASUREMENT OF ANGLES

[75] Inventors: Christian Flambard, Gagny; Alain Lambert, Creil; Miguel Sancho Pavon, Gouvieux, all of France

[73] Assignee: Centre Technique des Industries Mechaniques, Senlis, France

[22] Filed: Sept. 27, 1974

[21] Appl. No.: 510,022

[30] Foreign Application Priority Data

Mar. 19, 1974  France .................... 74.09182

[52] U.S. Cl. .................... 73/67.7; 73/67.8 R
[51] Int. Cl.² .................... G01N 29/04
[58] Field of Search ........... 73/67.7, 67.8 R, 67.8 S, 73/67.9

[56] References Cited
UNITED STATES PATENTS

| | | | |
|---|---|---|---|
| 2,645,933 | 7/1953 | Arenberg | 73/67.8 R |
| 3,837,218 | 9/1974 | Flambard et al. | 73/67.8 R |

FOREIGN PATENTS OR APPLICATIONS

| | | | |
|---|---|---|---|
| 766,984 | 1/1957 | United Kingdom | 73/67.7 |

*Primary Examiner*—James J. Gill
*Attorney, Agent, or Firm*—Haseltine, Lake & Waters

[57] ABSTRACT

Angles and angular displacements of ultrasonic beams are measured by using a probe to transmit the beam to a point on a surface, particularly the surface of material being subjected to non-destructive examination, from which the beam is reflected to a receiving probe which may or may not be the same device as the transmitting probe. The length of the path traversed by the beam is varied in accordance with a relationship determined as a function of the angular displacement of the beam from an axis normal to the surface, and the time taken to traverse the path is detected. The variation in the length of the path may be effected by adjusting the separation of the transmitting probe from the surface while the probe is being angularly adjusted to vary the angular displacement of the beam, a fixed mirror being provided to return the beam by way of the point to the probe. Alternatively an angularly adjustable transmitting probe may direct the beam to the point and a separate probe which is both axially and angularly adjustable arranged to receive the relfected beam. In a third alternative, the transmitting probe directs the beam to the point by way of an adjustable mirror, a fixed mirror being arranged to return the beam by way of the point and the adjustable mirror to the probe.

15 Claims, 10 Drawing Figures

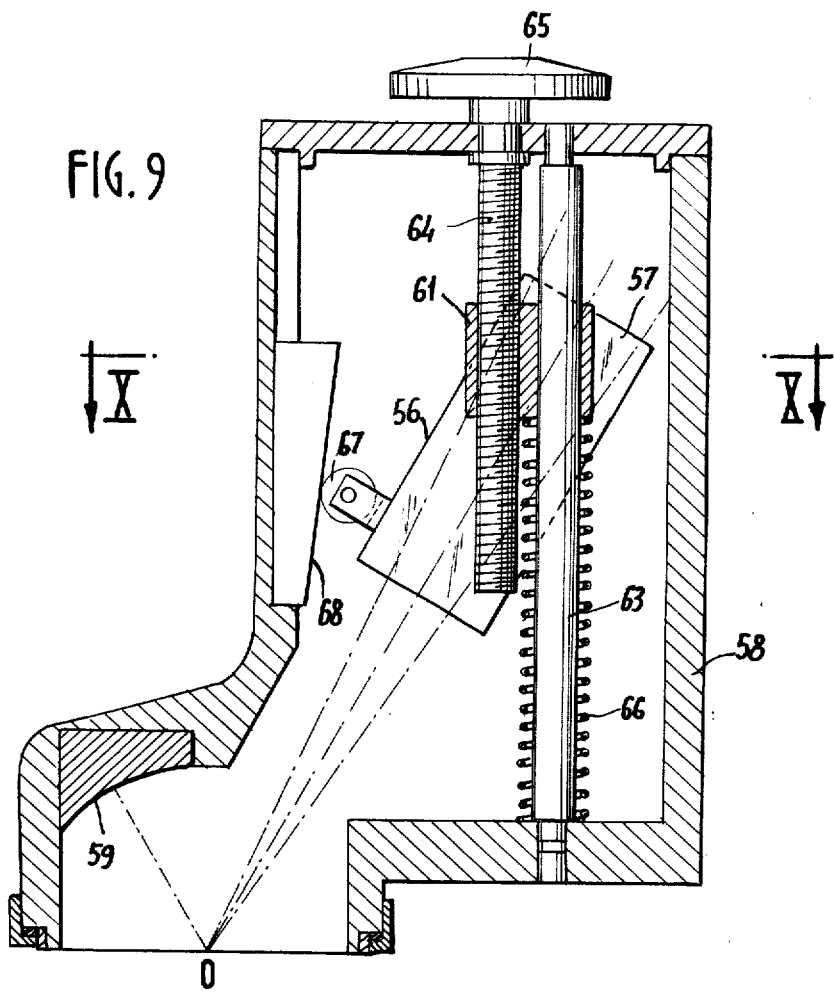
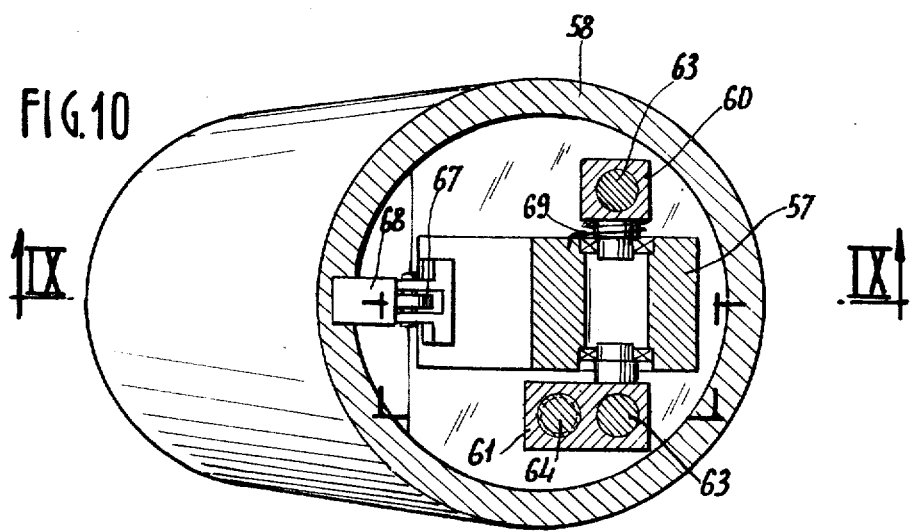

MEASUREMENT OF ANGLES

FIELD OF THE INVENTION

The present invention has for its subject a method and instrument enabling angular positions to be detected and angles or angular displacements to be measured, more particularly for the non-destructive examination of materials with the aid of ultrasonic waves.

DESCRIPTION OF THE PRIOR ART

In the non-destructive examination of materials by ultrasonic waves, use is made of mechanical oscillations at high frequencies in the ultrasonic range with the object of obtaining information concerning the properties and faults of materials being studied. This information is derived from the analysis of the phenomena of transmission, reflection, diffraction, diffusion or radiation of the ultrasonic waves, and in order to carry out observation of these phenomena it is very often necessary to be able to impart suitable orientation to the probes which transmit and/or receive the ultrasonic beam and to detect or measure the angles between the direction of propagation of the ultrasonic waves and the surface of the materials being examined.

In conventional techniques, these angles are determined by the orientation of the probes and measured independently of observation of the ultrasonic beam properly speaking. Such measurements require highly accurate equipment which is delicate to put into use.

SUMMARY OF THE INVENTION

As compared to these known techniques, the invention has in particular the advantage of enabling angles to be very accurately measured, of making the results of measurements easier to use, and of simplifying the corresponding apparatus, especially in the case in which it is required to determine the angles corresponding to the maxima and minima of ultrasonic energy. For these purposes, the invention resides essentially in linking the length of the path followed by the ultrasonic beam, which can be measured by the time whichit takes to traverse this path, to the angular position of the ultrasonic beam.

The present invention thus has for its subject a method for detecting angular positions of an ultrasonic beam, characterized in that the length of the path followed by the ultrasonic beam is varied in accordance with a relationship determined as a function of the angular displacements of the beam, and in that the time taken by the ultrasonic beam to traverse said path is detected. The beam is preferably deflected at a substantially fixed point corresponding to the center of the angular displacements, more particularly by reflection on a definite surface.

The process according to the invention is applicable in a most especially advantageous fashion to the non-destructive examination of materials by analyzing the phenomena already indicated above. The angular positions detected are then in general those of an ultrasonic beam transmitted to a substantially fixed point on the material or received from a substantially fixed point thereon.

However, the process is likewise beneficially applicable to the detection or measurement of angles in any other field. One particular method of using the process then resides in imparting to an ultrasonic beam an angular displacement corresponding to an angle to be measured, in measuring the variation in the time taken by the ultrasonic beam to traverse the path for said angular displacement, and in deducing therefrom the value of the angle by the definite relationship imparted to the variations in the length of the path as a function of the angular displacements of the beam.

In all cases, it is advantageous to use the process within a relatively small range of angular displacements, for which it is then easier to work out a simple relationship, close to a linear relationship; for example, between the variations in the length of the path and the angular displacements of the beam.

For non-destructive examination of materials, the process is especially applicable to the use of experiments in which an incident ultrasonic beam is caused to be reflected at a substantially fixed point on the surface of the material to be examined, and the variations in energy of the reflected beam are observed as a function of the angle of incidence. In particular, it thus makes it possible to determine the critical angular positions of the incident beam beyond which the longitudinal or transverse waves undergo total reflection, and the angular positions for which the Rayleigh waves are produced by picking out the angles corresponding to the maxima and minima characteristic of the variations in reflected energy.

The present invention likewise covers instruments which enable the process defined above to be used for its various functions.

Such an instrument may advantageously comprise at least one moving element in the path of the ultrasonic wave enabling the beam to be angularly displaced and-/or the length of the path to be varied, which element may be a beam-transmitting and/or receiving probe or an intermediate beam-deflector element for example, a mirror, a prism, or the surface itself of a material to be examined.

Angular displacement may be imparted to the beam, and variation to the length of the path of the ultrasonic beam, by way of two different moving elements whereof the movements are suitably linked. However, it is generally more advantageous to associate with the same moving element means which enable combined rotational and translational movements to be communicated to it, such movements being themselves capable of setting up the definite relationship between angular displacement of the beam and variation of the length traversed by the ultrasonic beam.

DESCRIPTION OF THE DRAWINGS

The invention will be clearly understood from the following description and examining the appended drawings, which illustrate solely by way of example a few ways of carrying out the process and constructing the device which constitute the subject of the invention. In the drawings:

FIG. 9 depicts another instrument seen in longitudinal part-section, the sections being on the line IX—IX in FIG. 10, and FIG. 10 is a transverse section on the line X—X in FIG. 9.

The various instruments hereinafter described make it possible to observe an ultrasonic beam while it is being angularly displaced by imparting a concomitant variation to the length of the path traversed by the ultrasonic waves from transmission to reception in accordance with a relationship determined as a function of the angular displacements of the beam by measuring the time taken by an ultrasonic pulse to traverse this path. In general, reference is made to the preferred case in which the ultrasonic beam used is transmitted in the direction of a fixed point on the surface of a material and in which the beam is received after having been reflected at least once on this surface.

The ultrasonic waves are produced in the form of pulses by a probe generally consisting of a piezo-electric ceramic subjected to periodical electric charges. Reception may be carried out by a different probe, or by the same probe in the time-intervals separating successive transmissions of pulses.

Figure 1:
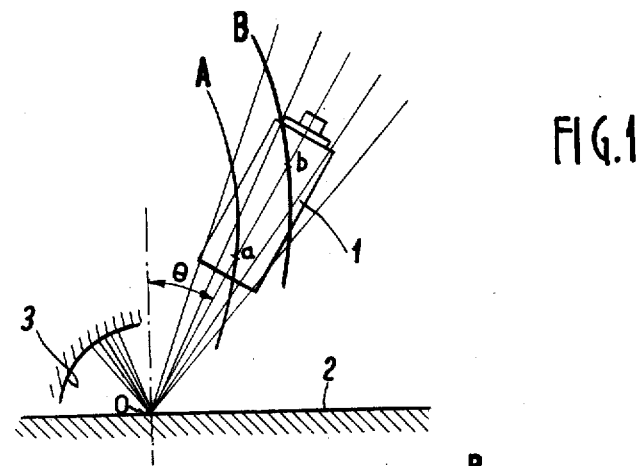
FIG. 1 diagrammatically illustrates a first form of the invention involving the use of a single probe for transmitting and receiving ultrasonic waves.

Thus the device diagrammatically illustrated in FIG. 1 comprises a single probe 1, both transmitting and receiving. The axis of the probe is represented by two points $a$ and $b$ which, by the construction of the device, are caused to move on two curves A and B respectively, which are such that:

the direction $a$–$b$ always passes through a fixed point O on a surface 2 of a test piece generally formed by the surface of a piece to be studied;

the distance O–$a$ is a simple and known function of the angle $\theta$ of incidence on the surface 2, more particularly a linear function.

A spherical or cylindrical mirror 3 centered on the point O enables the ultrasonic waves reflected by the surface 2 to be turned back in the opposite direction to the probe 1.

Measurement of the time taken by a pulse to proceed from the probe to the mirror and back enables the distance traversed by the waves to be defined, and the angle $\theta$ to be accurately deduced therefrom. The speed of propagation of the waves in the medium traversed between the probe 1, the surface 2 and the mirror 3, generally a liquid coupling medium, is assumed to be known, and said coupling medium may be chosen so that the speed at which the ultrasonic waves are propagated is practically insensitive to variations in temperature. The relationship set up between angular displacements of the probe 1 by rotation about the point O, and the variation in its distance from the point O, that is to say the variation in the length of the path followed by the ultrasonic waves being perfectly defined by the construction of the instrument, the angles may be determined by the measured transit time with very great accuracy. Thus if the axis of the probe rotates through 10°, which would be accompanied by a variation of 30 mm in the distance from the probe to the surface 2, in the case of acoustic coupling provided by water, measurement of the transit time makes it possible to perceive variations in distance of 0.05 mm, corresponding to an angular displacement of 1' of arc.

Figure 2:
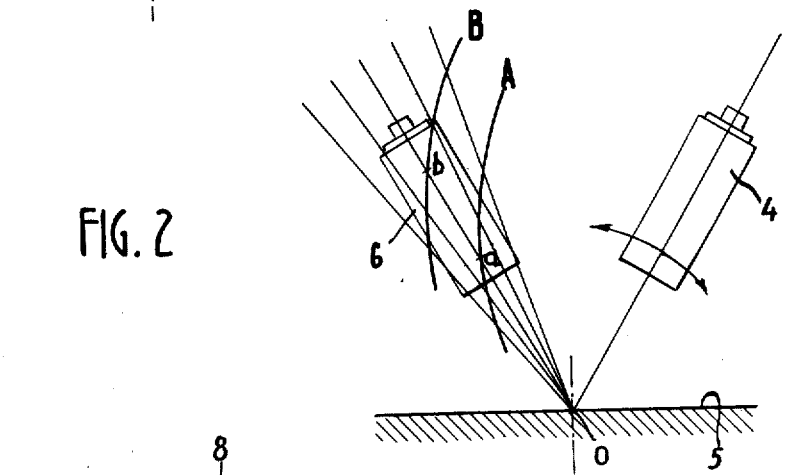
FIG. 2 diagrammatically illustrates a second form of the invention involving the use of two different probes for transmitting and receiving the ultrasonic waves.

The instrument diagrammatically illustrated in FIG. 2 comprises two probes. A transmitting probe 4 is mounted so that its axis can pivot about the fixed point O on the surface of a test piece 5. A receiving probe 6, whereof the axis is likewise centred on the point O, is mounted in movable fashion so that two points $a$ and $b$ which represent its axis, are constrained to move in accordance with curves A and B defined like those of FIG. 1.

In the case being considered, the transmitting probe is displaced independently of the receiving probe, and when the transmitting probe is in a definite position the receiving probe is then displaced in order to search for the position in which it receives ultrasonic pulses of maximum energy corresponding to the beam reflected from the transmitting probe by the surface of the test piece. Measurement of the time taken by an ultrasonic pulse to proceed from the transmitting probe to the receiving probe after reflection on this surface makes it possible, as in the preceding case, to deduce the length of the path traversed by the ultrasonic waves, and therefore the angular positions of the probes.

As a variant of this instrument, the transmitting and receiving probes may be caused to move symmetrically to one another with respect to the normal to the surface of the test piece.

When the angular displacement of the probe of FIG. 1 or of the two probes of FIG. 2 is small, the curves A and B may be replaced by rectilinear trajectories. The apparatus may then be considerably simplified with respect to that which is necessary in order to provide curved trajectories.

In other ways of using the invention, the probe or probes used for transmitting and receiving the ultrasonic beam may be fixed, the concomitant variations in the angle of incidence of the beam and in the length of the path of the ultrasonic waves then being produced by one or more moving elements in the path of the beam, such as elements for reversing or deflecting the beam.

Figure 3:
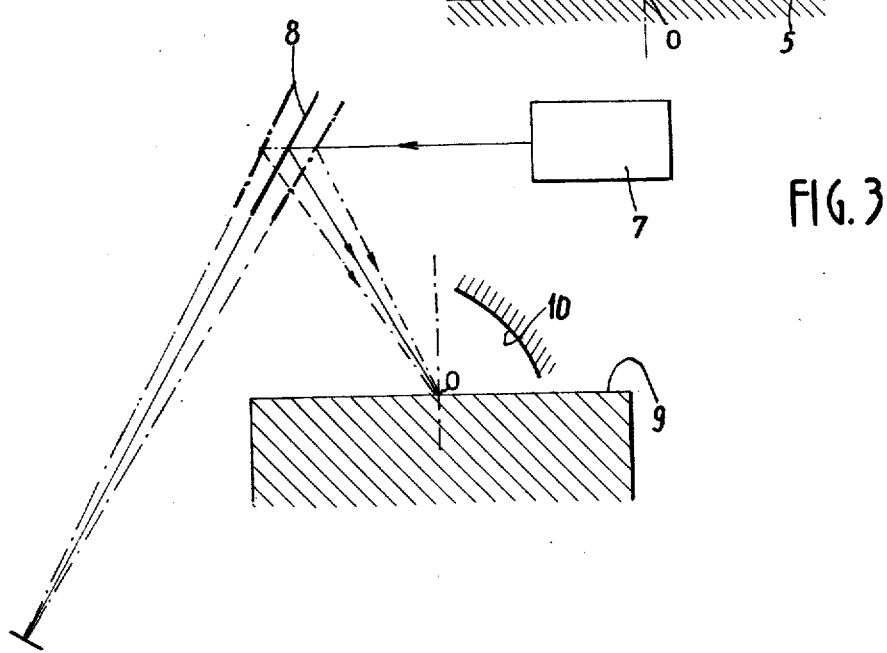
FIG. 3 diagrammatically illustrates a moving-mirror device.

Thus the instrument of FIG. 3 comprises a fixed probe 7, both transmitting and receiving, a moving-mirror 8 suitable for reflecting the ultrasonic waves transmitted by the probe 7 in the direction of the fixed point O on the surface 9, and a spherical or cylindrical fixed mirror 10, centred on the point O, which enables the beam reflected at O by the surface 9 to be turned back on itself.

In the case illustrated in FIG. 3, the moving-mirror 8 is a simple plane mirror capable of being driven in a rotational movement, which is illustrated in the Figure by different positions of the same mirror. In such a device, rotation of the mirror 8 may impart a slight displacement to the point aimed at on the surface 9 of the test piece. However, for relatively small useful angular displacements (of the order of a few degress) of the axis of the incident beam, the displacement of the beam on the surface of the piece about the point O remains in practice much less than the wavelength of the waves used (for example of the order of 0.05 mm), and therefore negligible.

In the case in which the incident beam must be able to undergo large angular displacements, for example of the order of one or more tens of degrees, a more complicated system for displacing the moving element may be used so that the point O where the beam is reflected on the surface of the test piece will remain substantially fixed.

Figure 4:
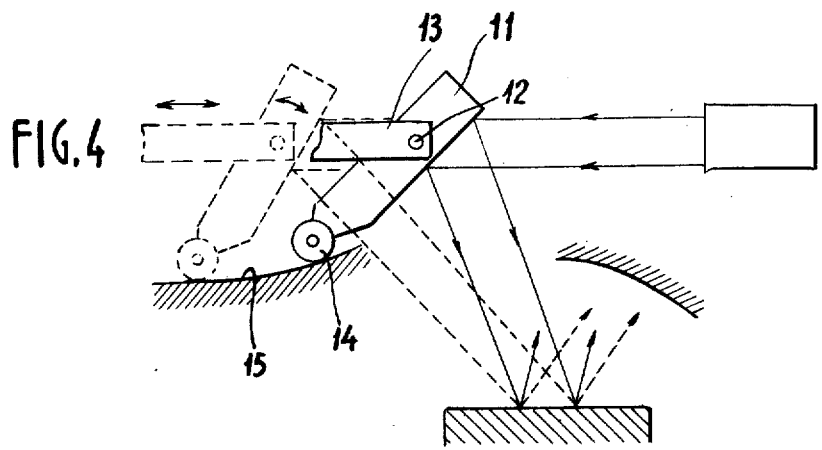
FIG. 4 depicts a means for displacing a moving-mirror.

Such a more complicated system is illustrated by FIG. 4. In the latter, a mirror 11, which functions in relation to the ultrasonic beam in the same manner as the mirror 8 of FIG. 3, pivots about a spindle 12 at the end of an acutating rod 13. This rod makes it possible to displace the spindle 12 linearly on the axis of the probe which transmits and receives the ultrasonic beam. The mirror 11 carries a roller 14, which is caused to move on a cam 15 while the rod 13 is moving, so as to make the mirror rotate about its spindle 12. The profile of the cam 15 is determined so as to impart a suitable combined translational and rotational movement to the mirror.

Whatever the means of transmitting and detecting the ultrasonic beam, and the means used in order to impart the angular displacement to the incident beam, the device is particularly useful for the non-destructive examination of materials by observing variations in the energy of the reflected beam as a function of the angle of incidence on the surface of the material. These variations make it possible to determine the critical angles of incidence of the various modes of oscillation set up in the material for the incident wave, these angles being those for which the longitudinal and transverse refracted waves are at an angle equal to 90° with the normal to the surface, and those for which the Rayleigh waves are produced.

The variations in energy of the reflected wave are measured by the detector probe. They may be made visible on an oscilloscope whereof the time scale may be so determined as to express directly the value of the angle of incidence $\theta$, since the path length of the ultrasonic waves, and therefore the transit time, is a known function of this angle of incidence.

Figure 5:
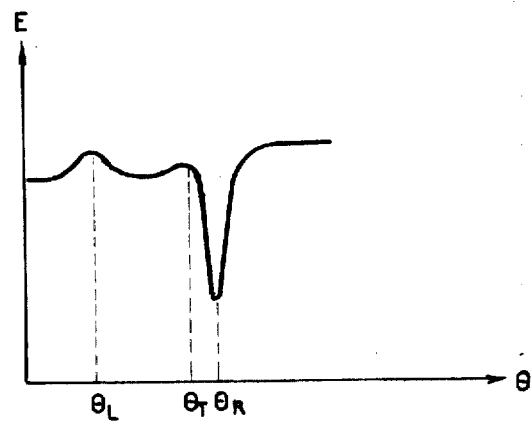
FIG. 5 depicts a curve showing the variation in energy of a reflected beam as a function of the angle of incidence, and illustrates the use of the invention in the non-destructive examination of materials.

FIG. 5 illustrates the variations in energy E of the received ultrasonic pulses as a function of the angle of incidence $\theta$. It shows the maxima and minima corresponding to the various critical angles of incidence, that is to say $\theta_L$ for the longitudinal waves, $\theta_T$ for the transverse waves and $\theta_R$ for the Rayleigh waves.

From the values of these three angles, and knowing the speed at which the waves are propagated in the coupling medium traversed by the beam that is to say, $V_i$, it is possible to deduce the speeds of propagation corresponding to each of the three different modes of propagation of the waves by the relationships:

Longitudinal waves $\quad V_L = \dfrac{V_i}{\sin \theta_L}$

Transverse waves $\quad V_T = \dfrac{V_i}{\sin \theta_T}$

Rayleigh waves $\quad V_R = \dfrac{V_i}{\sin \theta_R}$

In general, however, it will be sufficient to measure the angles $\theta_L$ and $\theta_R$ since the maximum corresponding to the transverse waves is not clear, while the corresponding speed of propagation may be calculated from the other two.

Knowledge of the speeds of propagation corresponding to the different modes of propagation of the waves enables known methods of calculation to be used in order to deduce the mechanical characteristics of the material being examined, in particular Young's modulus and Poisson's ratio.

Moreover, measurement of the speed of propagation of the Rayleigh waves makes it possible to determine, by methods which are likewise known, the thickness of a covering or the depth of a treatment which imparts modifications to the surface layers of a material, for example thermal and thermochemical hardening treatments.

A description will now be given, with more details, of two particular forms of instrument according to the invention, enabling these critical angles of incidence on the surface of a material to be measured.

Figure 6:
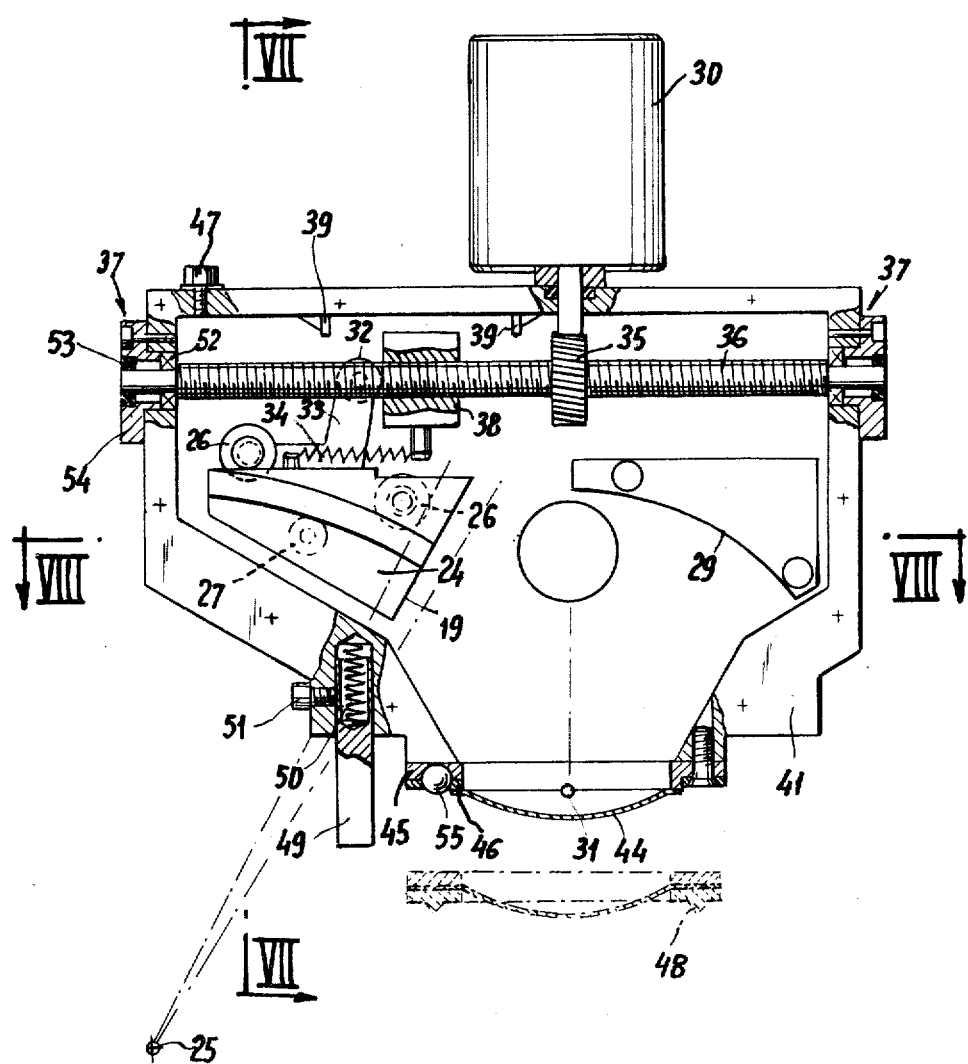
FIG. 6 depicts in part-section one particular form of an instrument according to the invention.
Figure 7:
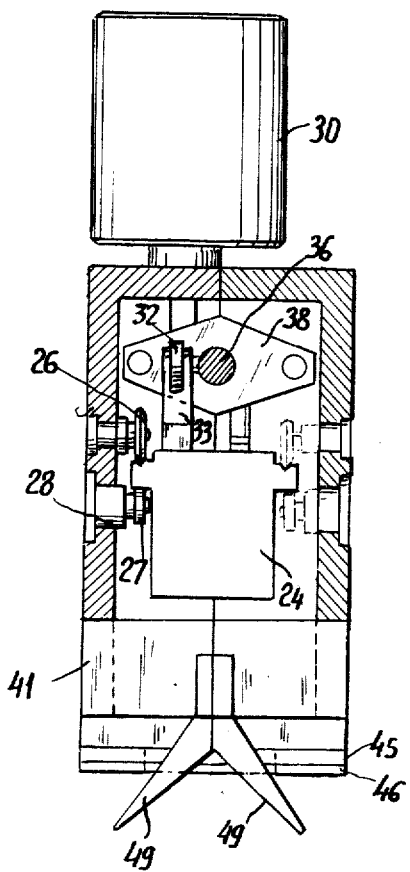
FIG. 7 shows a section on the line VII—VII in FIG. 6.
Figure 8:
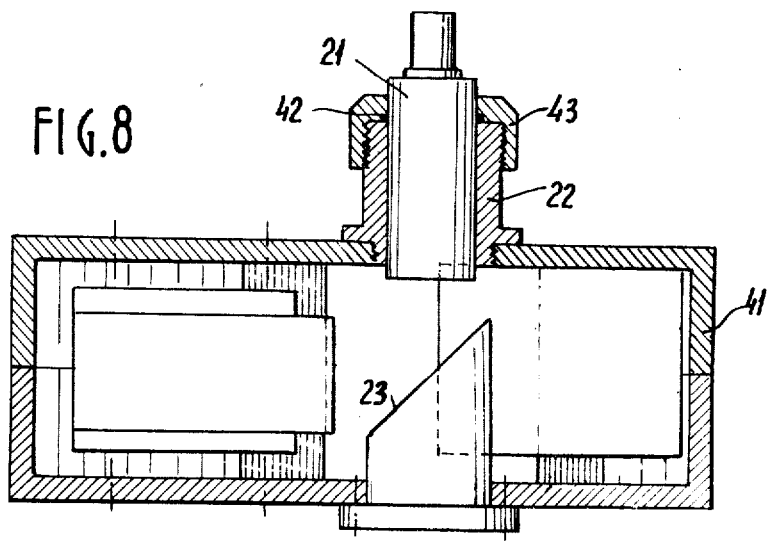
FIG. 8 shows a section on the line VIII—VIII in FIG. 6.

In the instrument illustrated in FIGS. 6, 7 and 8, an ultrasonic probe 21 (FIG. 8) is held in a sleeve 22 fast with one of the faces of a shell 41 containing the device. In the opposite face of the shell there is a cylindrical piece whereof the axis coincides with that of the probe 21, and wherein there is a mirror 23 cut at 45° to the axis. This mirror enables the device to be adjusted by self-collimation. Rotation of the cylindrical piece through 90° about the axis enables the ultrasonic beam transmitted by the probe 21 to be reflected in a direction either perpendicular to the surface of a piece of material being examined, i.e., to the point 31 of FIG. 6, or in the direction of a mirror 19 formed on a moving member 24.

In operation, the mirror 23 is so disposed as to direct the ultrasonic beam towards the mirror 19, and the latter directs the beam to the peice to be examined, to the fixed point 31, at an incidence which may be varied by displacement of the moving member 24.

The variation is imparted to the angle of incidence of the beam by rotation of the member 24 about an imaginary axis 25 in a guide device. This device comprises two rollers 26 on fixed axes. The rollers bear against two symmetrical cylindrical bosses machined on the moving member 24. An opposing roller 27 holds the member 24 against the rollers 26; it is mounted on an eccentric spindle 28 (FIG. 7), which enables the member 24 to be set while the device is being assembled.

A cylindrical mirror 29 is so disposed as to receive the ultrasonic beam reflected by the surface of the piece being examined at 31. It is fixed, and its axis is parallel to the plane of the surface of the piece being examined, and passes through the point 31 on this surface. The mirror 29 thus enables the ultrasonic beam to be returned on a reverse path to the probe 21, which is a transmitting and receiving probe.

The movable mirror 19 is set in motion by a motor 30. The latter imparts rotation to a worm 36 by way of a group of pinions 35. The worm is held in the shell 41 by two units 37 comprising a bearing race 52 and a fluid-tight packing 53 mounted in a ring 54.

The work 36 carries a co-operating nut 38 which is driven in a translational movement by rotation of the worm. The moving member 24 carrying the mirror 19 is caused to follow faithfully the translational movement of the nut 38 by way of roller 32 mounted on an arm 33 fast with the member 24 and a return spring 34 which holds the roller 32 against the nut. Two abutments 39 carried by the shell 41 limit the stroke of the nut 38, and therefore that of the moving member 24.

The shell of the instrument is designed to be filled with a liquid, which enables acoustic coupling to be made between the probe and the piece to be examined. Fluid-tightness is provided:

at the level of the probe 21, by a toroid packing 42 clamped to the latter by a ring 43;

at the location of the aperture of the shell, brought to bear against the test piece to be examined, by a fine elastic diaphragm 44 transparent to the ultrasonic waves, held by a ring 45 on to a ring 46 surrounding the aperture.

Plugs 47 on the top of the shell of the instrument, enable it to be filled with liquid and relieved of air. Pressure is applied to the liquid, which causes the elastic diaphragm 44 to be deformed by bulging outwards as far as the test piece, when in position, permits, by driving the probe 21 into its sleeve 22. The elements 44, 45 and 46 as a whole may be easily removed and replaced, which allows for the use of interchangeable units adapted to the configuration of the pieces to be examined.

Thus in order to examine a plane surface the rings 45 and 46 as illustrated in FIG. 6 are so formed as to contain three balls 55, which bear against the precision-machined reference surfaces on the ring 46. These balls go beyond the ring 45, and serve to locate the piece to be examined to bear against the instrument.

In the case of a cylindrical surface, it is possible to use the interchangeable unit which is also illustrated in FIG. 6, and which comprises two knife edges 48 whereof the tips are in a plane containing a generatrix of the cylindrical surface of the piece to be examined. The cylinder is accurately positioned with respect to the instrument by two V-shaped feet 49 on stems that slide in two bores in the shell 41, and are loaded by compression springs 50. The stems are secured in adjusted positions in the bores by screws 51. In the case in which the piece being examined exhibits a warped surface, the rings 45 and 46 may be so moulded so as to adapt them to the pieces to be examined. Other specific forms of positioning device may also be used.

The operation of the instrument illustrated in FIGS. 6, 7 and 8 is clear from the foregoing description. It may be added that the system for clamping the probe 21 enables a probe of suitable characteristics to be chosen in each case, more particularly in regard to frequency-response or beam-size characteristics.

As has already been indicated, the setting of the instrument with respect to the surface of the test piece may be checked with the aid of the return mirror 23 tilted to reflect the beam directly on to the surface of the piece being examined; the reflected energy received by the probe is at a maximum when the piece is properly set.

In order to carry out measurements, the electric motor 30 is driven by direct current whereof the polarity may be reversed. The amplitude of the echoes reflected by the surface of the piece is measured for example on the screen of a cathode-ray tube.

These measurements may be put to use, for example, in determining the depth of thermal treatment in the pieces being examined. The measurement is first of all made on an untreated piece, for which the extreme position corresponding to the critical angle at which the surface waves (Rayleigh waves) start is determined. An abac trace starting from this point of origin makes it possible to determine the critical angles corresponding to measurements subsequently made on treated pieces, and to deduce therefrom by direct reading the value of the depth of treatment.

The instrument illustrated in FIGS. 9 and 10 comprises a single return mirror, which is fixed, and the variations in angle of incidence and in the length of the path of the ultrasonic waves are produced by manual displacement of the ultrasonic probe. A transmitting and receiving probe 56 is held in a movable sleeve 57 inside the shell 58 of the instrument. It transmits the waves to the surface of the piece to be examined, at the point O. A cylindrical mirror 59 enables the beam reflected by the surface of the piece to be returned to the probe 56.

The sleeve 57 carries guide members 60 and 61, which are mounted on the sleeve by way of bearing races, and which slide on two columns 63 fixed vertically in the device. One of the guide members 61 contains a nut co-operating with a worm 64, which may be rotated by a manual control knob 65 accessible from outside the shell 58. A spring 66, bearing against the bottom of the shell and against the member 61, results in any play which there may be being taken up.

The sleeve 57 moreover carries a roller 67, which is held against a fixed cam 68 by the force developed by a spring 69 bearing against the guide member 60.

The device thus described makes it possible, as does the preceding one, to vary the length of the path of the ultrasonic waves as a function of the angular displacements of the probe whereof the axis if kept orientated towards the point O, the measurements being made and the results being put to use in the same manner as hereinbefore.

The invention must naturally not be limited to the particular forms which have been described above by way of example. It must be more particularly understood that the length of the path of the ultrasonic waves may be varied, and the beam may be angularly displaced, by action on different moving elements, which in each case may take the form either of a probe for transmitting and/or receiving the ultrasonic waves or of an intermediate moving beam-deflector element. In the same way, the invention has been described more particularly in relation to its use in the non-destructive examination of materials, but the devices described may, without departing from the scope of the invention, be adapted to the measurement of angles in any other field; it is then sufficient to impart to the beam an angular displacement corresponding to the angle to be measured.

We claim:

1. A method of measuring the angular position of an ultrasonic beam comprising the steps of: projecting the ultrasonic beam by a transmitting probe onto a fixed point of a surface, receiving the beam from said point by a receiving probe, varying the length of the path traversed by the ultrasonic beam from said transmitting probe to said receiving probe in accordance with a relationship determined as a function of the angular displacement of the transmitted beam with respect to said surface, and detecting the time taken by the ultrasonic beam for traversing said path.

2. A method of measuring the angular position of an ultrasonic beam relatively to a surface to which the beam is transmitted and from which it is reflected, comprising projecting the ultrasonic beam onto said surface by a probe, receiving the reflected beam by a probe, varying the length of the path traversed by the ultrasonic beam from said transmitting probe to said receiving probe in accordance with a relationship determined as a function of the angular displacement of the beam from an axis normal to said surface, and detecting the time taken for the ultrasonic beam to traverse said path.

3. A method according to claim 2, in which said transmitting probe and said receiving probe are constituted by one and the same instrument.

4. A method according to claim 2, in which for all angular positions of the ultrasonic beam, the beam is reflected from a substantially fixed point on said surface.

5. A method according to claim 2, in which the ultrasonic beam is caused to undergo an angular displacement related to said angular position so that the length of said path traversed by the ultrasonic beam varies, while the time taken for the ultrasonic beam to traverse said path is measured, and the value of said required angular position from said relationship deduced.

6. A method according to claim 2, wherein material to be non-destructively examined is arranged to present said surface, and wherein said transmitting probe is directed to a point which is fixed for all angular positions of the ultrasonic beam and from which the beam is reflected to a mirror that returns the beam by way of said point, to said transmitting probe, said transmitting probe serving also as said receiving probe.

7. A method according to claim 2, wherein material to be non-destructively examined is arranged to present said surface, and wherein said transmitting probe is adjusted to set the angle of the beam relatively to a fixed axis normal to said surface, to be reflected to said receiving probe, and wherein said receiving probe is angularly adjusted with respect to said normal axis while its distance from said surface is varied in accordance with said relationship.

8. A method according to claim 2, in which said time taken to traverse said path is determined as a function of the variation of the energy of the beam detected after transmission along said path.

9. An ultrasonic equipment comprising means for transmitting an ultrasonic beam towards a fixed point, means for receiving the beam from said fixed point, means for angularly displacing the beam with respect to a fixed axis about said fixed point, means for imparting a variation in length to the path traversed by said beam from said transmitting means through said fixed point to said receiving means in accordance with a relationship determined as a function of angular displacements of the beam and means for detecting the time taken by the beam to traverse said path.

10. An instrument according to claim 9, in which said transmitting means is arranged to transmit the beam to a point on a surface beyond the instrument and said receiving means is arranged to receive the beam after reflection at said point.

11. An instrument according to claim 9, in which said means for imparting variation in length to said path comprises means for displacing a probe in an axial and in an angular direction, said probe constituting one of said means for transmitting and receiving the beam.

12. An instrument according to claim 9, in which said means for imparting variation in length to said path comprises an intermediate element, between said transmitting and receiving means, for deflecting the beam.

13. An instrument according to claim 9, in which said transmitting means is arranged to transmit the beam to a point on a surface beyond the instrument and in which said angularly displacing means are arranged to adjust the angle of incidence of the beam on said surface, said receiving means being arranged to receive the beam after reflection and the instrument further comprising means for making variations in energy of the reflected beam directly visible as a function of said angle of incidence.

14. An instrument according to claim 9, comprising a movable member carrying a mirror interposed in said path of the ultrasonic beam, said means for angularly displacing the beam and imparting a variation in length comprising further means for guiding said movable member along a curved track for varying the length of said path in relation to the angular displacement of the beam, and nut and worm means for moving said member along said track.

15. An instrument according to claim 9, comprising a movable member, said means for angularly displacing the beam and imparting a variation in length comprising further means for guiding said movable member along a straight track, screw mechanism for feeding said movable member along said track, a probe comprising said transmitting and receiving means pivotally mounted on said movable member, and cam means for varying the angular position of said probe on said movable member while being fed along said track.

* * * * *